United States Patent [19]

Watson et al.

[11] Patent Number: 4,520,220
[45] Date of Patent: May 28, 1985

[54] ALKYLATION OF AROMATICS EMPLOYING SILICALITE CATALYSTS

[75] Inventors: James M. Watson; James R. Butler; Cleve H. Forward, all of Big Spring, Tex.

[73] Assignee: Cosden Technology, Inc., Dallas, Tex.

[21] Appl. No.: 350,673

[22] Filed: Feb. 22, 1982

[51] Int. Cl.³ .............................................. C07C 2/68
[52] U.S. Cl. ................................................. 585/467
[58] Field of Search ........................................ 585/467

[56] References Cited

U.S. PATENT DOCUMENTS

| | | | |
|---|---|---|---|
| Re. 29,587 | 12/1978 | Argauer et al. | 208/111 |
| Re. 29,948 | 3/1979 | Dwyer et al. | 208/134 |
| 3,251,897 | 5/1966 | Wise | 585/455 |
| 3,716,596 | 2/1973 | Bowes | 585/467 |
| 3,751,504 | 8/1973 | Keown et al. | 585/523 |
| 3,751,506 | 8/1973 | Burress | 585/467 |
| 3,755,483 | 8/1973 | Burress | 585/467 |
| 3,884,835 | 5/1975 | Vaughan | 423/338 |
| 3,926,782 | 12/1975 | Plank et al. | 208/135 |
| 3,941,871 | 3/1976 | Dwyer et al. | 423/331 |
| 3,962,364 | 6/1976 | Young | 585/466 |
| 4,016,218 | 4/1977 | Haag et al. | 585/467 |
| 4,061,724 | 12/1977 | Grose et al. | 423/339 |
| 4,073,865 | 2/1978 | Flanigen et al. | 423/339 |
| 4,086,287 | 4/1978 | Kaeding et al. | 585/466 |
| 4,094,921 | 6/1978 | Kaeding et al. | 585/467 |
| 4,100,217 | 7/1978 | Young | 585/467 |
| 4,104,319 | 8/1978 | Kaeding | 585/454 |
| 4,107,224 | 8/1978 | Dwyer | 585/449 |
| 4,117,024 | 9/1978 | Kaeding | 585/466 |
| 4,117,026 | 9/1978 | Haag et al. | 585/467 |
| 4,127,616 | 11/1978 | Rodewald | 585/467 |
| 4,128,592 | 12/1978 | Kaeding | 585/466 |
| 4,136,128 | 1/1979 | Haag et al. | 585/467 |
| 4,148,713 | 4/1979 | Rollmann | 208/111 |
| 4,197,413 | 4/1980 | Kaeding et al. | 568/798 |
| 4,238,318 | 12/1980 | Kouwenhoven et al. | 585/409 |
| 4,270,017 | 5/1981 | Young | 585/437 |
| 4,283,306 | 8/1981 | Herkes | 252/432 |
| 4,309,275 | 1/1982 | Mulaskey | 585/648 |
| 4,309,276 | 1/1982 | Miller | 585/648 |

FOREIGN PATENT DOCUMENTS 80200495.2 5/1980 European Pat. Off. .

OTHER PUBLICATIONS

Fyfe et al., *Nature*, vol. 296, Apr. 8, 1982, pp. 530-533.
Fyfe et al., Chemistry Letters, 1983, The Chem. Soc. of Japan, pp. 1551-1554.
Thomas et al., Chemistry Letters, 1983, The Chem. Soc. of Japan, pp. 1555-1556.
"Silicalite, A New Hydrophobic Crystalline Silica Molecular Sieve", by Flannagan, et al., *Nature*, vol. 271, Feb., 1978.
"Chemical and Physical Properties of the ZSM-5 Substitutional Series", by Olsen, Haag and Lago, *Journal of Catalysis* 61, 390-396 (1980).
"Pentasil Family of Hig Silica Crystalline Materials", by J. T. Kokotailo and W. M. Meier, Chem. Society Special Publication 33, 133-139 (1980).
"Reactions On ZSM-5-Type Zeolite Catalysts", by J. R. Anderson, K. Foger, T. Mole, et al., *Journal of Catalysis*, 58, 114-130 (1979).

Primary Examiner—Curtis R. Davis
Attorney, Agent, or Firm—John K. Abokhair

[57] ABSTRACT

A process for alkylating aromatic substrates is disclosed which includes contacting the aromatic substrate with an alkylating agent in a reaction zone at temperatures of from about 350° C. to about 500° C. in the presence of a crystalline silica polymorph silicalite catalyst material.

11 Claims, 1 Drawing Figure

ALKYLATION OF AROMATICS EMPLOYING SILICALITE CATALYSTS

TECHNICAL FIELD

This invention relates to a process for alkylating aromatic hydrocarbons by contacting same under specified conversion conditions in the presence of silicalite type catalysts. In another aspect, this invention relates to a process for alkylation of aromatic substrates with alkylating agents, and in particular, ethylene. A further aspect of this invention relates to a process for maintaining the activity, as measured by conversion of aromatic substrate materials to alkyl substituted aromatic compounds, of silicalite catalysts employed in alkylation processes, thereby extending cycle life of these catalytic materials as used in alkylation processes.

BACKGROUND OF INVENTION

Hydrocarbon conversion processes, and in particular, alkylation of aromatic substrates are the basis for the production of a wide variety of useful petrochemicals. For example, alkyl substituted aromatics such as ethylbenzene and ethyltoluene are useful as feedstocks which, upon further conversion, produce important styrene and vinyltoluene monomers essential to the production of a variety of styrenic polymer materials. At present, many alkylation processes include processing steps wherein the aromatic substrates which are to be converted are contacted under alkylation conditions in the presence of catalyst materials. Both single and multiple catalyst bed processes are well known in the art. One factor which affects the efficiency of the alkylation with respect to the production of desired products, is the type of catalyst employed and the specific properties of the catalyst. One such important property is the selectivity of the catalyst to the desired product. Production of unwanted by-products can be very detrimental because some of the by-products may be very difficult, or impossible, to separate from the desired product. Thus, as an example of selectivity, it is desirable that a catalyst used in the production of ethylbenzene produce a maximum amount of that desired alkyl aromatic and a minimum amount of xylenes, which is very difficult to separate and is undesirable from a processing standpoint. A second property of catalysts used in alkylation processes is activity. The activity of a catalyst, i.e., the capability of a catalyst to convert the raw feed materials to products, has two aspects. First, the catalyst performance is rated on the basis of what percentage of the feed materials will be converted into products of some kind. Normally, this measurement is made by determining the amount of raw feed materials which have passed through the process without combining or otherwise reacting. Obviously, the higher the conversion rate, the better the activity of the catalyst material. The second aspect of activity is the maintenance of a high conversion rate with passage of time. Deactivation of catalysts is one major problem in catalytic alkylation processes since if high conversion rates cannot be maintained over a long period of time, expensive catalyst changeouts and/or regeneration procedures must be performed which reduce the efficiency of the overall process. As used herein, the term "stability" refers to the relative activity of the catalyst material as a function of time.

The use of zeolite type catalysts, of both natural and man-made varieties, in hydrocarbon conversion processing has been known for some time. Recently, aluminosilicate type zeolite catalysts, including those known as "ZSM-5" catalyst materials have been reported to be suitable for hydrocarbon conversion processes and, in particular, for the alkylation of aromatic substrates. One problem with these types of catalysts, however, is that they are subject to rapid deactivation in the presence of even small amounts of water. Thus, when using such catalysts, it is sometimes necessary to reduce the moisture content of feedstock materials prior to their introduction into a conversion zone.

Another type of catalyst material, which can be characterized as a crystalline silica polymorph, prepared in accordance with specified procedures and known generically as "silicalite" has been discovered to be useful in hydrocarbon conversion processes. These catalysts are not subject to deactivation in the presence of steam and, in some cases, as set forth in our now abandoned co-pending application Ser. No. 06/255,882, steam actually enhances the selectivity (apparently from a reduction of especially troublesome by-product, e.g. xylenes) and stability of these materials during alkylation. However, as is the case with other catalyst materials, obtaining high selectivity and maintaining high conversion rates over commerically acceptable periods of time would be especially desirable.

SUMMARY OF THE INVENTION

It has now been discovered that excellent product selectivity as well as high conversion rates and low rates of deactivation (i.e., increased stability) can be achieved when employing silicalite type catalyst materials without the need to specially treat or otherwise modify the catalysts themselves or co-feed any material other than the feedstocks which are to be converted. Specifically, it has been discovered that by controlling the temperature during alkylation processes which employ silicalite catalysts within a range of from about 350° C. to 500° C., better stability can be attained and better selectivity, demonstrated by reduced production of some of the most troublesome by-products, obtained.

Thus, in general, the present invention provides a method for alkylating aromatic substrates by reacting these materials in the presence of a crystalline silica polymorph catalyst of the silicalite type under conversion conditions which comprise temperatures in the range of from about 350° C. to about 500° C. In the preferred embodiment of the present invention, aromatic substrates such as benzene and toluene are alkylated with alkylating agents such as ethylene, propylene, etc. by contacting the aromatic substrate and alkylating agent in the presence of a crystalline silica polymorph silicalite catalyst under alkylation conditions which include reaction temperatures of from about 350° C. to about 500° C. An especially preferred temperature range is from about 400° C. to about 475° C. The silicalite catalyst material need not be modified in any manner and water in the form of steam may be co-fed as an option, if desired. By operating within the specified temperature range, the catalytic activity of the unmodified silicalite material can be maintained and excellent stability and conversion rates can be achieved. Further, lesser amounts of xylene and undesirable polyalkyls are produced due to good selectivity of the catalysts under the specified reaction conditions.

DETAILED DESCRIPTION

Figure 1:
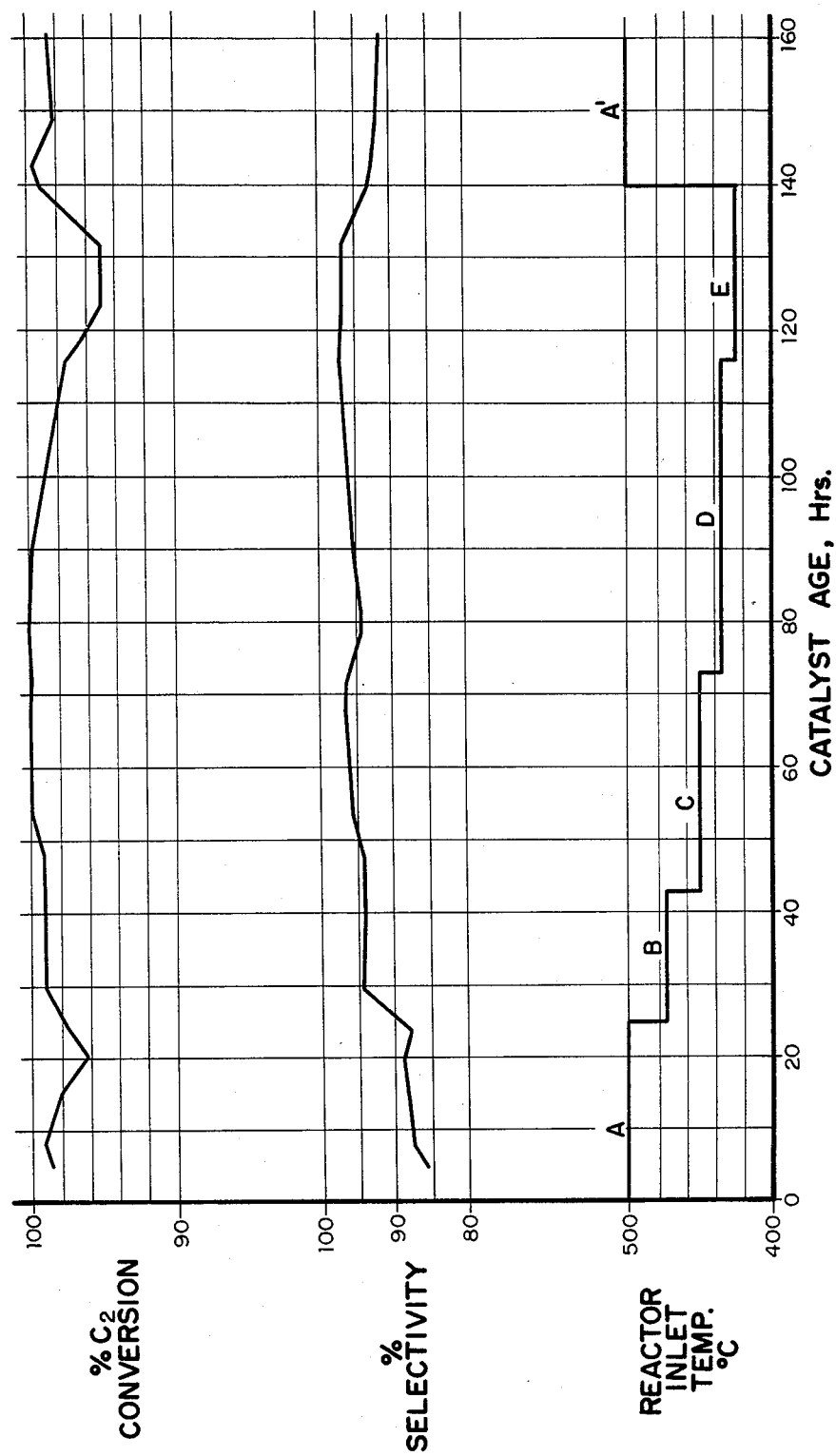

The alkylation process of the present invention basically comprises the steps of feeding aromatic substrates and alkylating agents to a conversion zone containing a crystalline silica polymorph silicalite type catalyst wherein the reactants are allowed to contact the catalyst under controlled conversion temperatures, pressures, and residence times. Specifically, temperatures in the range of from about 350° C. to about 500° C. Preferred reactants include aromatic feedstocks such as benzene, toluene, ethylbenzene, napthalene and similar compounds which can be converted by alkylation upon contact with reactive alkylating agents such as ethylene and propylene, for example.

The process can be carried out using a variety of process equipment, including a reactor vessel which defines an alkylation zone and contains the silicalite catalyst material. Either single or multiple catalyst beds can be employed in the reaction zone. The hydrocarbon reactants such as benzene and ethylene, for example, can be admixed and preheated prior to introduction into the reaction zone where they contact the catalyst beds under reaction conditions further specified hereinbelow. If desired, steam can be admixed with the reactants prior to introduction to the reaction zone. After a controlled residence time within the reaction zone, the converted hydrocarbon charge passes out of the reactor where the desired products are collected by cooling and other standard recovery techniques.

The mole ratio of aromatic substrates to alkylating agents will be controlled in accordance with the desired reaction products. Pressures and weight hourly space velocity of the reactants passing through the conversion zone will be the major factors affecting residence time (and therefore contact time with the silicalite catalyst material) within the zone. The temperatures specified herein are measured as inlet temperatures of the conversion zone during steady-state operation.

The catalyst material employed by the process of the subject invention is a true crystalline silica material as opposed to a zeolitic material, which, by definition, is a silicate of aluminum and either sodium or calcium, or both, which demonstrates ion exchange capacity. The crystalline silica materials used as catalysts in the present invention are silica polymorphs whose structures have been designated as "silicalite". These materials, in contrast to aluminosilicate zeolites, demonstrate no appreciable ion exchange properties since $AlO_4^-$ tetrahedra do not comprise a portion of the crystalline silica framework. Aluminum may be present in these silicalite catalyst materials, however, its presence is a result of impurities in the silica source used to prepare the material and silicalite containing such alumina or other metal oxide impurities can in no sense be considered to be a metallosilicate. Further description and methods for preparing silicalite type catalysts are set forth in U.S. Pat. No. 4,061,724, the entire disclosure of which is incorporated herein by reference.

In addition to the physical and chemical distinctions between crystalline silica polymorph silicalite type catalysts and aluminosilicate zeolites, several functional distinctions are also apparent as regards the use of these materials as hydrocarbon conversion catalysts. For example ZSM-5 type aluminosilicate zeolites when employed in alkylation reaction are reported to rapidly lose catalytic activity in the presence of even minor amounts of water. As noted hereinabove, the crystalline silica polymorph silicalite materials of the present invention are useful as hydrocarbon conversion catalysts even in the presence of steam and, in most instances, performance of the process can be enhanced through the use of steam co-feed.

In a preferred embodiment, aromatic feedstocks are alkylated by contacting same with alkylating agents in the presence of silicalite catalyst materials under reaction conditions which comprise temperatures of from about 350° C. to about 500° C. By employing these conditions, increased activity is obtained and improved stability, i.e., retention of activity with time, can be achieved. Steam co-feed can be employed, if desired. Generally, the reaction of aromatic feedstocks with alkylating agents is run with a substantial molar excess of aromatic substrate in order to reduce the incidence of polyalkylation. Desirably, the mole ratio of aromatic substrate to the alkene feed will lie between about 2:1 and about 20:1, and preferably between about 3:1 and about 16:1. Operating pressures will normally be between about atmospheric pressure and about 25 atmospheres and preferably between about 10 and 15 atmospheres.

The process of the subject invention, which employs silicalite type catalysts in combination with specified temperature ranges, provides an especially efficient procedure for producing ethylbenzene and ethyltoluene. The increased catalytic stability obtainable through the use of temperatures in the range of from about 350° C. to about 500° C. allows the cycle length of the catalyst to be extended, which, of course, is of great commercial advantage. When employing the subject process to produce ethylbenzene or ethyltoluene from benzene and toluene aromatic feedstocks, the preferred silicalite catalysts are those having a crystallite size of less than about 8 microns and silica to alumina ratios of at least about 200. Preferred reactant ratios (aromatic/alkene) are from about 4:1 to about 20:1 with the preferred aromatic feed WHSV's ranging from about 50 to about 150. Further, operating pressures between atmospheric and 25 atmospheres can be used with a range of from about 10 to about 15 being preferred. Reaction conditions include, of course, temperatures at the reaction zone inlet of from about 350° C. to about 500° C.

If steam co-feed is desired, the preferred amount is from about 20,000 to about 60,000 parts per million, based on the amount of aromatic compound with 40,000 parts per million steam co-feed being preferred.

The process of the subject invention can be further exemplified through a study of the following examples which are not intended to limit the subject invention in any manner.

EXAMPLE I

Benzene and ethylene are introduced into a reaction zone containing a bed of silicalite catalyst material having a particle size of between 12 and 20 mesh and a bed depth of approximately 8.25 cm. The benzene to ethylene molar feed ratio is approximately 16:1. Operating conditions include a benzene WHSV of about 110, pressure of about 11 atmospheres and inlet temperature of approximately 420° C. The product stream from the alkylation reaction zone is analyzed by gas chromotography. The catalyst activity is determined both at the start and at the end of the trial according to the following formula:

% conversion =

$$\frac{\text{moles desired alkyl aromatic compound}}{\text{moles of reactive alkene fed to reactor}} \times 100\%$$

The selectivity is determined according to the following formula:

$$\text{selectivity} = \frac{\text{weight desired alkyl aromatic compound}}{\text{total product weight}} \times 100\%$$

At a catalyst age of approximately 13.3 hours, conversion is approximately 100% and selectivity is approximately 96.3%. At a catalyst age of 23.3 hours, conversion is approximately 95.6% and selectivity has increased to 99%. Under these conditions, this data indicates that deactivation of the catalyst, as calculated by the following formula:

$$\frac{(\text{Initial Conversion Percent} - \text{Final Conversion Percent})}{(\text{Initial Time} - \text{Final Time})}$$

was approximately 0.44%/hr loss of activity.

EXAMPLE II

In this example, the procedure of Example I is repeated except that the temperature of operation is changed to 325° C. Measurements are taken at a catalyst age of approximately 25.3 hours at which time conversion is approximately 16.5% and selectivity is approximately 91%. A second measurement is taken at a catalyst age of approximately 29.3 hours and conversion has dropped to approximately 11.9% while selectivity has stayed approximately the same. Under these conditions, the data indicates that there is approximately a 1.13%/hr loss of activity, about threefold that which was obtained using the temperature range of the process of the subject invention.

EXAMPLE III

The procedure of Example I is duplicated in all respects, including the use of a temperature of 420° C. The catalyst sample employed is the same as that used in Examples I and II above. Measurements are taken at 31.3 hours catalyst age and indicate that conversion is at a rate of 69.3% with selectivity at approximately 98.25%. A second measurement is taken at 41.3 hours and conversion is recorded at 64.4% with selectivity remaining approximately the same. This data indicates that stability of the catalyst has increased over operation at the lower temperature range of Example II, and that in fact the catalyst has resumed a lower rate of deactivation (approximately 0.49%/hr loss).

Table 1, set forth below, summarizes the data presented in Examples I through III above and demonstrates that by operating at approximately 420° C., significantly higher conversion and stability can be achieved in hydrocarbon conversion processes employing silicalite catalysts.

TABLE 1

| Example | Catalyst Age, hrs. | Temp. °C. | Initial Conv. | Final Conv. | Rate of Deactivation | Selectivity |
|---|---|---|---|---|---|---|
| I | 13.3–23.3 | 420 | 100% | 96.3% | 0.37% | 96.3–99% |
| II | 25.3–29.3 | 325 | 16.5% | 11.9% | 1.15% | 91% |
| III | 31.3–41.3 | 420 | 69.3% | 64.4% | 0.49% | 98.2% |

EXAMPLE IV

In this example, ethyltoluene is produced from a feedstock of toluene and ethylene fed to the alkylation zone in a molar ratio of approximately 18:1. Three separate runs are performed in which the inlet reaction temperature is varied from approximately 475° C. to 460° C. and finally, to approximately 450° C. In each instance, however, pressures of approximately 11 atmospheres, toluene WHSV's of 130 and steam in an amount of 40,000 ppm based on the weight of toluene is employed. The results of these three runs are set forth below in Table 2.

TABLE 2

| Catalyst Age, hrs. | Temp. °C. | Initial Conv. | Final Conv. | Deactivation Rate | Selectivity |
|---|---|---|---|---|---|
| 0–24 | 475 | 97.9% | 89.7% | 0.34% | 94.5% |
| 24–49 | 460 | 89.7% | 82.3% | 0.29% | 97.1% |
| 49–71 | 450 | 79.4% | 78.0% | 0.046% | 97.9% |

This indicates that deactivation rates as low as 0.06%/hr are obtainable when conversion conditions include temperatures within the range of 450° C. to approximately 475° C. at the reactor inlet.

EXAMPLE V

In this example, ethyltoluene is prepared by feeding toluene and ethylene in a molar ratio of 18:1 to a reaction zone containing a catalyst bed of silicalite catalyst approximately 8 cm deep, the catalyst having a mesh size between approximately 12 and 20. During this experiment a constant toluene WHSV of 130 and pressure of approximately 11 atmospheres is employed. The temperature over the entire run (which lasted approximately 160 hours) is varied between 500° C. and 425° C. at the reaction zone inlet. Selectivity of the process as well as its conversion as a function of catalyst age and temperature are set forth graphically in FIG. 1.

From a study of FIG. 1, it can be seen that conversion rates of greater than approximately 95% were maintained over the entire catalyst age of approximately 160 hours. This demonstrates that by operating within the specified reaction conditions, silicalite catalysts can be employed to produce ethyltoluene and will maintain useful cycle lifes.

One of ordinary skill in the art upon reading the above specification and examples will appreciate that the process of the subject invention can be modified or adapted in a variety of ways. All such modifications or adaptations which fall within the scope of the appended claims are intended to be covered thereby.

We claim:

1. A process for alkylating aromatic substrates with alkylating agents comprising passing these reactants in the absence of steam cofeed through a reaction zone containing a crystalline silica polymorph silicalite catalyst under conversion conditions including reaction zone inlet temperatures of from about 350° C. to about 500° C.

2. The process of claim 1 wherein said conversion conditions further comprise pressures of from about atmospheric to about 25 atmospheres.

3. The process of claim 2 wherein said reaction zone inlet temperatures are from about 400° C. to about 475° C.

4. A process for alkylating aromatic substrates selected from the group consisting of benzene and toluene comprising contacting said substrates with an alkylating agent, in the absence of steam cofeed in the presence of a crystalline silica polymorph silicalite catalyst under alkylation conditions which include reaction inlet temperatures of from about 350° C. to about 500° C.

5. The process of claim 4 wherein said alkylating agent is ethylene.

6. The process of claim 5 wherein the mole ratio of aromatic substrate to ethylene is from about 2:1 to about 20:1.

7. The process of claim 4 wherein said alkylation is carried out at pressures of from about atmospheric to about 25 atmospheres.

8. The process of claim 4 wherein said reaction inlet temperatures are from about 400° C. to about 475° C.

9. A method for reducing the rate of loss of activity of crystalline silica polymorph silicalite catalyst during alkylation processes in the presence of said silicalite catalyst and not employing steam cofeed comprising employing conversion conditions which include reaction temperatures in the range of from about 350° C. to about 500° C.

10. The method of claim 9 wherein said alkylation process comprises the alkylation of benzene or toluene with ethylene.

11. The method of claim 9 wherein said reaction inlet temperature are from about 400° C. to about 475° C.

* * * * *